(12) United States Patent
Biewer et al.

(10) Patent No.: US 11,141,518 B2
(45) Date of Patent: Oct. 12, 2021

(54) SMART CONNECTOR FOR A MEDICAL DEVICE

(71) Applicant: Fresenius Medical Care Holdings, Inc., Waltham, MA (US)

(72) Inventors: John Aaron Biewer, Waltham, MA (US); Kulwinder S. Plahey, Martinez, CA (US)

(73) Assignee: Fresenius Medical Care Holdings, Inc., Waltham, MA (US)

(*) Notice: Subject to any disclaimer, the term of this patent is extended or adjusted under 35 U.S.C. 154(b) by 170 days.

(21) Appl. No.: 16/009,407

(22) Filed: Jun. 15, 2018

(65) Prior Publication Data

US 2019/0381230 A1 Dec. 19, 2019

(51) Int. Cl.
*A61M 1/28* (2006.01)
*G16H 40/63* (2018.01)

(52) U.S. Cl.
CPC ............ *A61M 1/282* (2014.02); *G16H 40/63* (2018.01); *A61M 2205/3313* (2013.01); *A61M 2205/3331* (2013.01); *A61M 2205/3334* (2013.01); *A61M 2205/3368* (2013.01); *A61M 2205/3569* (2013.01); *A61M 2205/36* (2013.01); *A61M 2205/505* (2013.01); *A61M 2205/6072* (2013.01); *A61M 2209/086* (2013.01)

(58) Field of Classification Search
CPC ........ A61M 1/28; A61M 1/282; A61M 1/166; A61M 2205/3331; A61M 2205/3334; A61M 2205/3372; A61M 2205/6072; A61M 2205/3368; A61M 2205/36; A61M 2209/086; A61M 2209/088; A61M 1/285; A61M 2205/3313; A61M 2205/3569; A61M 2205/505; G16H 40/63
See application file for complete search history.

(56) References Cited

U.S. PATENT DOCUMENTS

2006/0289342 A1   12/2006   Sugioka et al.
2009/0078047 A1*  3/2009    Dam .................... G01N 29/222
                                                            73/606

(Continued)

FOREIGN PATENT DOCUMENTS

WO   WO 2013/141896 A1   9/2013
WO   WO 2017/062923 A1   4/2017

*Primary Examiner* — Amber R Stiles
*Assistant Examiner* — Alexandra Lalonde
(74) *Attorney, Agent, or Firm* — Muirhead and Saturnelli, LLC

(57) ABSTRACT

A sensor assembly measures characteristics of a fluid entering or exiting a patient via a catheter. The sensor assembly includes a flow tube that accepts the fluid at a first end thereof expels the fluid at a second end thereof, a plurality of sensors disposed about the flow tube, the sensors including at least one temperature sensor that measures temperature of the fluid and at least one pressure sensor that measures pressure of the fluid, and a connector that connects the sensor assembly to the catheter. The sensors may also include a clarity sensor, a conductivity sensor, a flow sensor, and/or an air detector. The sensor assembly may also include a wireless communication device that provides wireless communication. The sensor assembly may communicate with a dialysis machine via a network. The dialysis machine may be a peritoneal dialysis machine.

10 Claims, 5 Drawing Sheets

(56) References Cited

U.S. PATENT DOCUMENTS

| | | | |
|---|---|---|---|
| 2009/0149776 A1* | 6/2009 | Adams | A61B 5/0059 |
| | | | 600/584 |
| 2009/0275881 A1* | 11/2009 | Lo | G16H 20/40 |
| | | | 604/28 |
| 2011/0066006 A1 | 3/2011 | Banet et al. | |
| 2011/0172545 A1 | 7/2011 | Grudic et al. | |
| 2012/0095537 A1 | 4/2012 | Hall et al. | |
| 2012/0308431 A1* | 12/2012 | Kotsos | A61M 1/1686 |
| | | | 422/3 |
| 2013/0204098 A1 | 8/2013 | Chamney et al. | |
| 2013/0267883 A1 | 10/2013 | Medrano | |
| 2013/0296772 A1 | 11/2013 | Albalat | |
| 2014/0018727 A1 | 1/2014 | Burbank et al. | |
| 2016/0199559 A1* | 7/2016 | Glaser | G01L 19/14 |
| | | | 210/321.71 |
| 2016/0287773 A1* | 10/2016 | Lattimore | A61M 1/166 |
| 2018/0043081 A1* | 2/2018 | Lura | A61M 1/1656 |
| 2018/0110913 A1* | 4/2018 | Loderer | G01F 1/668 |

* cited by examiner

SMART CONNECTOR FOR A MEDICAL DEVICE

TECHNICAL FIELD

This application relates to sensors for medical devices and more particularly to sensors that determine operating parameters for medical devices.

BACKGROUND

Dialysis machines are known for use in the treatment of renal disease. Two types of dialysis methods are hemodialysis (HD) and peritoneal dialysis (PD). During hemodialysis, the patient's blood is passed through a dialyzer of a hemodialysis machine while also passing dialysate through the dialyzer. A semi-permeable membrane in the dialyzer separates the blood from the dialysate within the dialyzer and allows diffusion and osmosis exchanges to take place between the dialysate and the blood stream. During peritoneal dialysis, the patient's peritoneal cavity is periodically infused with dialysate or dialysis solution. The membranous lining of the patient's peritoneum acts as a natural semi-permeable membrane that allows diffusion and osmosis exchanges to take place between the solution and the blood stream. Automated peritoneal dialysis machines, also called PD cyclers, are designed to control the entire peritoneal dialysis process so that it can be performed at home, usually overnight, without clinical staff in attendance.

In many instances, a PD machine is located a significant distance from the patient (e.g., ten feet to twenty feet). As a result, important operating parameters, such as fluid temperature, may change as the fluid flows from the PD machine to the patient. That is, the temperature of the fluid may decrease from where the temperature is measured at the PD machine to where the fluid enters the patient. Fluid entering the patient at a temperature that is too cold (less than 37 degrees C.) causes patient discomfort. Overheating the fluid at the PD machine may not be an effective way to address this problem since fluid that is too hot (above 41 degrees C.) could damage the patient. In addition, it may be difficult to calculate an expected temperature drop between the PD machine and the patient, since such a calculation is based, at least in part, on the temperature of the location of the PD machine and the patient and on the flow rate. A similar situation occurs with fluid pressure since the fluid pressure may drop between the PD machine and the patient.

Accordingly, it is desirable to provide a mechanism that allows a more reliable determination of operating parameters such as temperature and pressure at the patient.

SUMMARY

According to the system described herein, a sensor assembly measures characteristics of a fluid entering or exiting a patient via a catheter. The sensor assembly includes a flow tube that accepts the fluid at a first end thereof expels the fluid at a second end thereof, a plurality of sensors disposed about the flow tube, the sensors including at least one temperature sensor that measures temperature of the fluid and at least one pressure sensor that measures pressure of the fluid, and a connector that connects the sensor assembly to the catheter. The sensors may also include a clarity sensor, a conductivity sensor, a flow sensor, and/or an air detector. The sensor assembly may also include a wireless communication device that provides wireless communication between each of the sensors and a dialysis machine. The sensor assembly may communicate with the dialysis machine via a network. The dialysis machine may be a peritoneal dialysis machine. The dialysis machine may stop automatic cycling in response to the temperature of the fluid exceeding a predetermined value and/or the pressure of the fluid exceeding a predetermined value. The plurality of sensors may be provided in a docking station and the flow tube may be a smart connector that is separate from the docking station. The smart connector and the docking station may include a coupling mechanism that identifies and mates the smart connector. The coupling mechanism may align particular sensors of the docking station with particular portions of the smart connector. The coupling mechanism may include a bar code, a chip, and/or physical features that align the smart connector with physical features of the docking station. Male and female portions of the physical features may have a matching, interlocking pattern.

According further to the system described herein, operating a dialysis machine includes determining pressure and temperature of fluid from the dialysis machine that is entering a patient via a catheter using a sensor assembly coupled to the catheter, the sensor assembly including sensors that are separate from the dialysis machine and the dialysis machine stopping automatic cycling in response to at least one of: the temperature of the fluid exceeding a predetermined value or the pressure of the fluid exceeding a predetermined value. The sensor assembly may include a flow tube that accepts the fluid at a first end thereof expels the fluid at a second end thereof and a plurality of sensors disposed about the flow tube. The plurality of sensors may be provided in a docking station and the flow tube may be a smart connector that is separate from the docking station. The smart connector and the docking station may include a coupling mechanism that identifies and mates the smart connector. The coupling mechanism may align particular sensors of the docking station with particular portions of the smart connector. The coupling mechanism may include a bar code, a chip, and/or physical features that align the smart connector with physical features of the docking station. Male and female portions of the physical features may have a matching, interlocking pattern. One of the plurality of sensors may measure clarity of fluid in the flow tube that flows from the patient to the dialysis machine. Operating a dialysis machine may also include the dialysis machine stopping automatic cycling in response to the fluid in the flow tube that is drained from the patient being cloudy.

BRIEF DESCRIPTION OF THE DRAWINGS

Embodiments and features of the system described herein are explained with reference to the several figures of the drawings, which are briefly described as follows.

DETAILED DESCRIPTION

Figure 1:
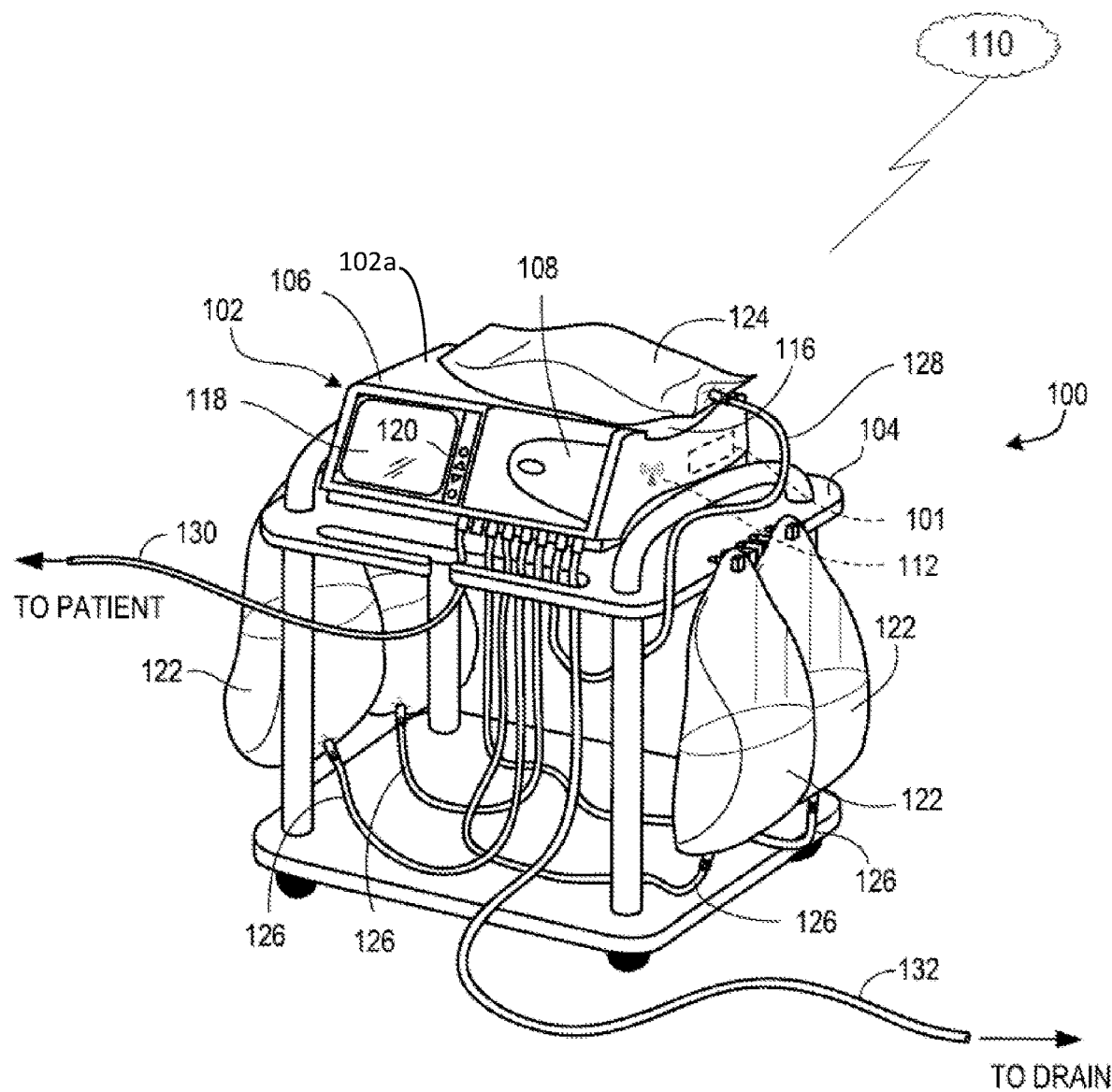
FIG. 1 illustrates an embodiment of a dialysis machine in a dialysis system configured in accordance with the present disclosure.

FIG. 1 shows an example of a medical device, implemented as a peritoneal dialysis (PD) system 100, that is configured in accordance with an embodiment of the system described herein. In some implementations, the PD system 100 may be configured for use at a patient's home (e.g., a home PD system). The PD system 100 may include a dialysis machine 102 (e.g. a PD machine, also referred to as a PD cycler) which, in some embodiments, may be seated on a cart 104. The dialysis machine 102 may include a housing 106, a door 108, and a cartridge interface for contacting a disposable PD cassette, or cartridge, when the cartridge is disposed within a compartment formed between the cartridge interface and the closed door 108. A heater tray 116 may be positioned on top of the housing 106. The heater tray 116 may be any size and shape to accommodate a bag of dialysate (e.g., a 5 L bag of dialysate). The dialysis machine 102 may also include a user interface such as a touch screen 118 and control panel 120 operable by a user (e.g., a caregiver or a patient) to allow, for example, set up, initiation, and/or termination of a PD treatment.

Dialysate bags 122 may be suspended from the sides of the cart 104, and a heater bag 124 may be positioned in the heater tray 116. Hanging the dialysate bags 122 may improve air management as any air is disposed by gravity to a top portion of the dialysate bag 122. Valves may be attached to a bottom portion of the dialysate bags 122 so fluid is drawn out and air delivery is minimized. Dialysate from the dialysate bags 122 may be transferred to the heater bag 124 in batches. For example, a batch of dialysate may be transferred from the dialysate bags 122 to the heater bag 124, where the dialysate is heated by the heating element. When the batch of dialysate has reached a predetermined temperature (e.g., approximately 98°-100° F., 37° C.), the batch of dialysate may be flowed into the patient. The dialysate bags 122 and the heater bag 124 may be connected to the cartridge via dialysate bag lines 126 and a heater bag line 128, respectively. The dialysate bag lines 126 may be used to pass dialysate from dialysate bags 122 to the cartridge during use, and the heater bag line 128 may be used to pass dialysate back and forth between the cartridge and the heater bag 124 during use. In addition, a patient line 130 and a drain line 132 may be connected to the cartridge. The patient line 130 may be connected to a patient's abdomen via a catheter and may be used to pass dialysate back and forth between the cartridge and the patient's peritoneal cavity during use. The drain line 132 may be connected to a drain or drain receptacle and may be used to pass dialysate from the cartridge to the drain or drain receptacle during use.

The touch screen 118 and the control panel 120 may allow a user to input various treatment parameters to the dialysis machine 102 and to otherwise control the dialysis machine 102. In addition, the touch screen 118 may serve as a display. The touch screen 118 may function to provide information to the patient and the operator of the PD system 100. For example, the touch screen 118 may display information related to a dialysis treatment to be applied to the patient, including information related to a prescription.

The dialysis machine 102 may include a processing module 101 that resides inside the dialysis machine 102, the processing module 101 being configured to communicate with the touch screen 118 and the control panel 120. The processing module 101 may be configured to receive data from the touch screen 118 the control panel 120 and sensors, e.g., temperature and pressure sensors, and control the dialysis machine 102 based on the received data. For example, the processing module 101 may adjust the operating parameters of the dialysis machine 102.

The dialysis machine 102 may be configured to connect to a network 110. The connection to the network 110 may be via a wired and/or wireless connection, as further discussed elsewhere herein. The dialysis machine 102 may include a connection component 112 configured to facilitate the connection to the network 110. The connection component 112 may be a transceiver for wireless connections and/or other signal processor for processing signals transmitted and received over a wired connection. Other medical devices (e.g., other dialysis machines) or components may be configured to connect to the network 110 and communicate with the dialysis machine 102. Although discussed herein principally in connection with a peritoneal dialysis machine, the system described herein may be used and implemented in connection with other types of medical devices having one or more displays, including home hemodialysis machines and/or other home medical devices.

Figure 2:
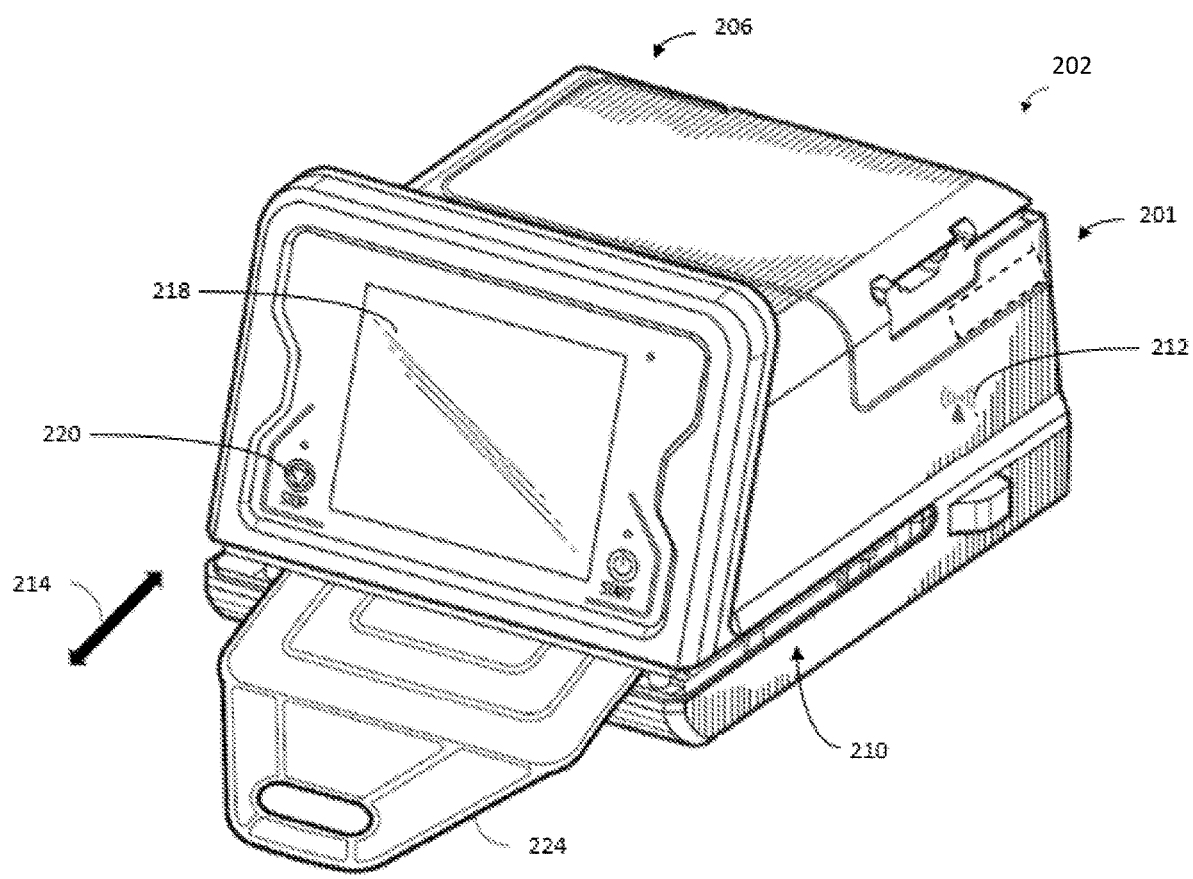
FIG. 2 illustrates another embodiment of a dialysis machine in accordance with the present disclosure.

FIG. 2 is a schematic illustration showing another embodiment of a dialysis machine 202 in accordance with the present disclosure. The dialysis machine 202 may be implemented in the peritoneal dialysis system 100 and may have at least some similar components as that of the dialysis machine 102, for example, including a housing 206, a processing module 201, a connection component 212, a touch screen 218, and a control panel 220 operable by a user (e.g., a caregiver or a patient) to allow, for example, set up, initiation, and/or termination of a PD treatment. The processing module 201 and the connection component 212 may be configured similarly to the processing module 101 and connection component 112 described above. However, instead of a heater tray being positioned on a top surface 102a of the housing as shown in FIG. 1 for the dialysis machine 102, one or more heating elements may be disposed internal to the machine 202. For example, a warmer pouch 224 may be insertable into an opening 210 in a direction indicated at arrow 214. In embodiments, the warmer pouch 224 may be configured so dialysate may continually flow through the warmer pouch (instead of transferred in batches) to achieve a predetermined temperature before flowing into the patient.

Figure 3:
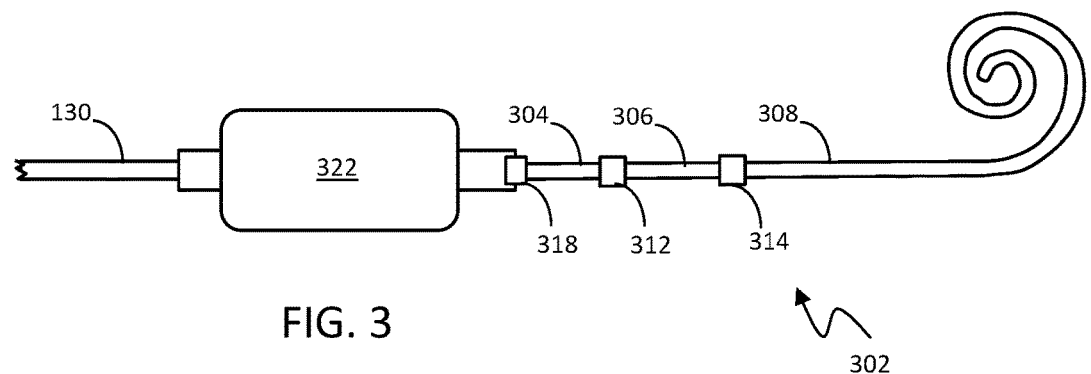
FIG. 3 illustrates a sensor assembly and a catheter in accordance with the present disclosure.

Referring to FIG. 3, a peritoneal dialysis catheter 302 is shown as including a first section 304, a second section 306, and a third section 308. Conventionally, the peritoneal dialysis catheter 302 is surgically implanted into a patient, usually at the abdomen, so that the first section 304 is located outside the patient, the second section 306 is located in the abdomen tissue of the patient, and the third section 308 is located in the peritoneal cavity of the patient. A subcutaneous cuff 312 between the first section 304 and the second section 306 and a peritoneal cuff 314 between the second section 306 and the third section 308 maintain the catheter 302 in place after surgical insertion. The third section 308 may include a plurality of holes (not shown) that facilitate passage of fluid between the catheter 302 and the peritoneal cavity to perform peritoneal dialysis where dialysis solution (water with salt and other additives) flows from the catheter 302 into the peritoneal cavity of the patient and, after a few hours, solution and wastes are drained out of the peritoneal cavity through the catheter 302.

The catheter 302 is coupled by a connector 318 to a first end of a sensor assembly 322. A second end of the sensor assembly 322 is coupled to the patient line 130 so that fluid flows between the patient and the dialysis machine 102 through the patient line 130, the sensor assembly 322 and the catheter 302. Fluid flows in to the patient and is drained out of the patient. The sensor assembly 322 contains a number of sensors (not shown in FIG. 3) that measure characteristics of fluid flowing through the sensor assembly 322, including temperature, pressure, flow rate, conductivity, clarity, and the presence of air. Information from the sensors may be provided to the dialysis machine 102 to be displayed by the dialysis machine 102 (i.e., via the touch screen 118) and/or may be used by the dialysis machine 102 to control operation thereof, as described in more detail elsewhere herein.

Figure 4:
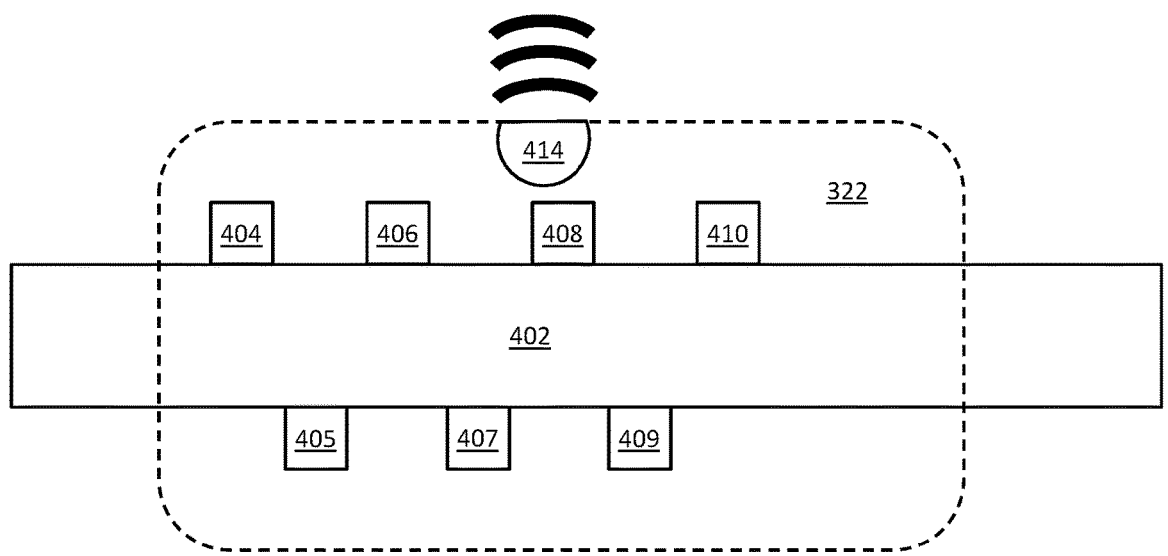
FIG. 4 illustrates a sensor assembly in more detail in accordance with the present disclosure.

Referring to FIG. 4, the sensor assembly 322 is shown in more detail as including a flow tube 402 that forms the first end of the sensor assembly 322 that connects to the patient line 130 (not shown in FIG. 4) and the second end of the sensor assembly 322 that connects to the catheter 302 (not shown in FIG. 4). Fluid from the dialysis machine 102 passes through the flow tube 402 into the patient in a first direction and fluid from the patient passes through the flow tube 402 in a second direction opposite to the first direction.

The sensor assembly 322 includes a clarity sensor 404, an IR temperature sensor 405, a conductivity sensor 406, a flow sensor 407, a contact temperature sensor 408, an air detector 409, and a pressure sensor 410. The clarity sensor 404 measures cloudiness of fluid from the patient passing through the flow tube 402. In some cases, particularly cloudy fluid passing out of the patient may be an indication of infection. The IR temperature sensor 405 measures temperature of fluid passing through the flow tube 402 using IR light and an IR transmissive window (not shown) placed in a portion of the flow tube 402 proximal to the sensor 405. The conductivity sensor 406 measure electrical conductivity of fluid passing through the flow tube 402, which may be a useful indication of chemical composition of the fluid, such as a concentration of salts in dialysate fluid passing from the dialysis machine 102 to the patient. The contact temperature sensor 408 may measure temperature of fluid passing through the flow tube 402 using, for example, conventional temperature contact sensors and possibly having a highly thermally conductive material in a corresponding portion of the flow tube 402. The flow sensor 407 measures flow of fluid from the dialysis machine 102 into the patient and the flow of fluid from the patient back to the dialysis machine 102.

In an embodiment herein, information from the contact temperature sensor 408 may be combined (e.g., averaged) with information from the IR temperature sensor 405 to improve accuracy of the temperature measurement of fluid in the flow tube 402. Note also that it may be possible to use information from the clarity sensor 404 to weight information from the IR temperature sensor 405 so that, for example, if the fluid is especially cloudy, information from the IR temperature sensor 405 may be considered less reliable and so may be given less weight when combined with information from the contact temperature sensor 408. The air detector 409 may detect the presence of (undesirable) air in fluid flowing from the dialysis machine 102 through the flow tube 402. The pressure sensor 410 may measure pressure of fluid flowing from the dialysis machine 102 through the flow tube 402. The sensor assembly 322 may receive power using any appropriate wired or wireless mechanism.

In some embodiments, the dialysis machine 102 may communicate with one or more of the sensors 404-410 using wires (not shown) coupled to the sensors 404-410. The wires may directly connect the one or more of the sensors 404-410 to the dialysis machine 102. Alternatively, the wires may connect to a wired communication module (not shown) that provides a multiplexed connection to the dialysis machine 102, possibly via the network 110, discussed above. Alternatively still, the sensor assembly 322 may include a wireless communication device 414 that provides wireless communication between each of the sensors 404-410 and the dialysis machine 102. Any appropriate wireless communication protocol may be used, including a connection through a secure Internet gateway to connect to a network that communicates with both the wireless communication device 414 and the dialysis machine, such as the network 110. The connection, network and data transmissions among components, both local and external, may be controlled and/other otherwise incorporated into a system that facilitates such functions with appropriate network infrastructure, and which may, in some implementations, be referred to as a connected health system. For further descriptions of systems for securely connecting, pairing and/or monitoring medical devices, such as in a connected health system, reference is made to US Pub. No. 20160206800 entitled "Remote Monitoring Interface Device and Mobile Application for Medical Devices" to Tanenbaum et al., U.S. Pat. No. 9,800,663 entitled "Associating Dialysis Accessories Using Near Field Communication" to Arrizza, US Pub. No. 20170087290 entitled "Short-Range Wireless Communication for a Dialysis System" to Medina et al., US Pub. No. 20170076069 entitled "Secure Network-Based System for Communication of Clinical Data" to Moissl et al., and U.S. Pat. No. 9,178,891 entitled "Remote Control of Dialysis Machines" to Wang et al., the disclosures of all of which are hereby incorporated by reference.

Figure 5:
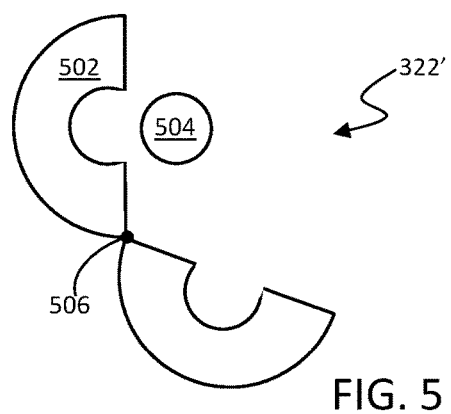
FIG. 5 illustrates an alternative embodiment of a sensor assembly that includes a docking station and a smart connector in accordance with the present disclosure.

Referring to FIG. 5, an alternative sensor assembly 322' includes two separate portions, a docking station 502 and a smart connector 504. The docking station 502 and the smart connector 504 may be generally tube-shaped, with longitudinal axes perpendicular to the view shown in FIG. 5. The docking station 502 may be in two parts that swing together on a hinge 506 to close around the smart connector 504. The docking station 502 includes sensors (not shown) similar to the sensors 404-410 discussed elsewhere herein and a mechanism for exchanging data with the dialysis machine 102, such as the wireless communication device 414, discussed above. The smart connector 504 is like the flow tube 402, discussed above, but may be separable from the docking station 502 so that, for example, the smart connector 504 is connected to the catheter 302 and/or the patent line 130 without necessarily including the docketing station 502 at all times while the system is operating.

Figure 6A:
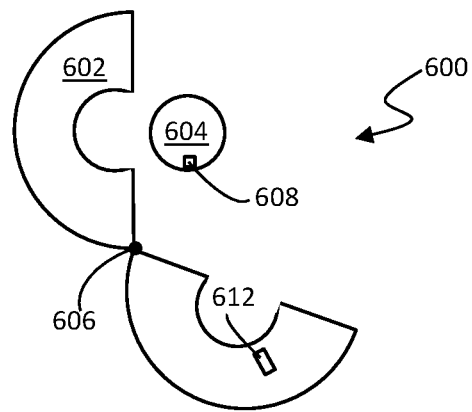
FIGS. 6A-6C illustrate alternative embodiments of a sensor assembly that includes a docking station and a smart connector in accordance with the present disclosure.

Referring to FIG. 6A, an alternative sensor assembly 600 includes two separate portions, a docking station 602 and a smart connector 604. The docking station 602 and the smart connector 604 may be generally tube-shaped, with longitudinal axes perpendicular to the view shown in FIG. 6A. The docking station 602 may be in two parts that swing together on a hinge 606 to close around the smart connector 604. The docking station 602 includes sensors (not shown) similar to the sensors 404-410 discussed elsewhere herein and a mechanism for exchanging data with the dialysis machine 102, such as the wireless communication device 414, discussed above. The smart connector 604 is like the flow tube 402, discussed above, but may be separable from the docking station 602 so that, for example, the smart connector 604 is connected to the catheter 302 and the patent line 130 without necessarily including the docketing station 602 at all times while the system is operating.

The smart connector 604 and the docking station 602 may include a coupling mechanism, such as a chip 608 and a chip reader 612, that identify and mate the smart connector 604 with the docking station 602. The chip 608 and the chip reader 612 guide a user to a particular alignment that aligns particular sensors of the docking station 602 with particular portions of the smart connector 604. For example, if the docking station 602 includes an IR temperature sensor like the IR temperature sensor 405 of the sensor assembly 322, described above, then the chip 608 and the chip reader 612 may direct the user to align the IR temperature sensor of the docking station with a clear window on the smart connector 604. Similarly, a connectivity sensor of the docking station 602 may be made to align with conductivity pads on the smart connector 604. In some embodiments, it is possible for the docking station 602 to have more sensor interfaces than the smart connector 604 so that some of the sensors of the docking station 602 remain unused, depending upon the configuration of the smart connector. In some cases, differently configured smart connectors may be used depending upon particular data being monitored for treatment and/or data used to control the dialysis machine 102.

Figure 6B:
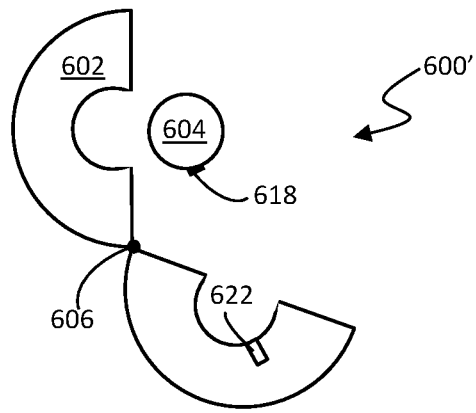
Figure 6C:
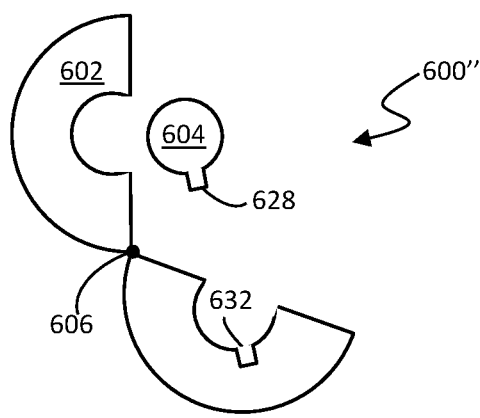

FIG. 6B illustrates an alternative embodiment of a sensor assembly 600' where the smart connector 604 includes a bar code label 618 superimposed thereon and the docking station 602 includes a reader 622 that may be used for alignment as described elsewhere herein. Similarly, FIG. 6C illustrates an alternative embodiment of a sensor assembly 600" where physical features are used for alignment. The smart connector 604 includes a male key portion 628 and the docking station 602 includes a female key portion 632 that may be used for alignment of the docking station 602 and the smart connector 604 as described elsewhere herein.

Note that, although discussed herein principally in connection with the peritoneal dialysis machine 102, the system described herein, including the sensor assemblies 322, 322', 600, 600', 600", and similar sensor assemblies may be used and implemented in connection with other types of dialysis machines, including hemodialysis machines, and generally other medical devices, including home hemodialysis machines and/or other home medical devices.

Figure 7:
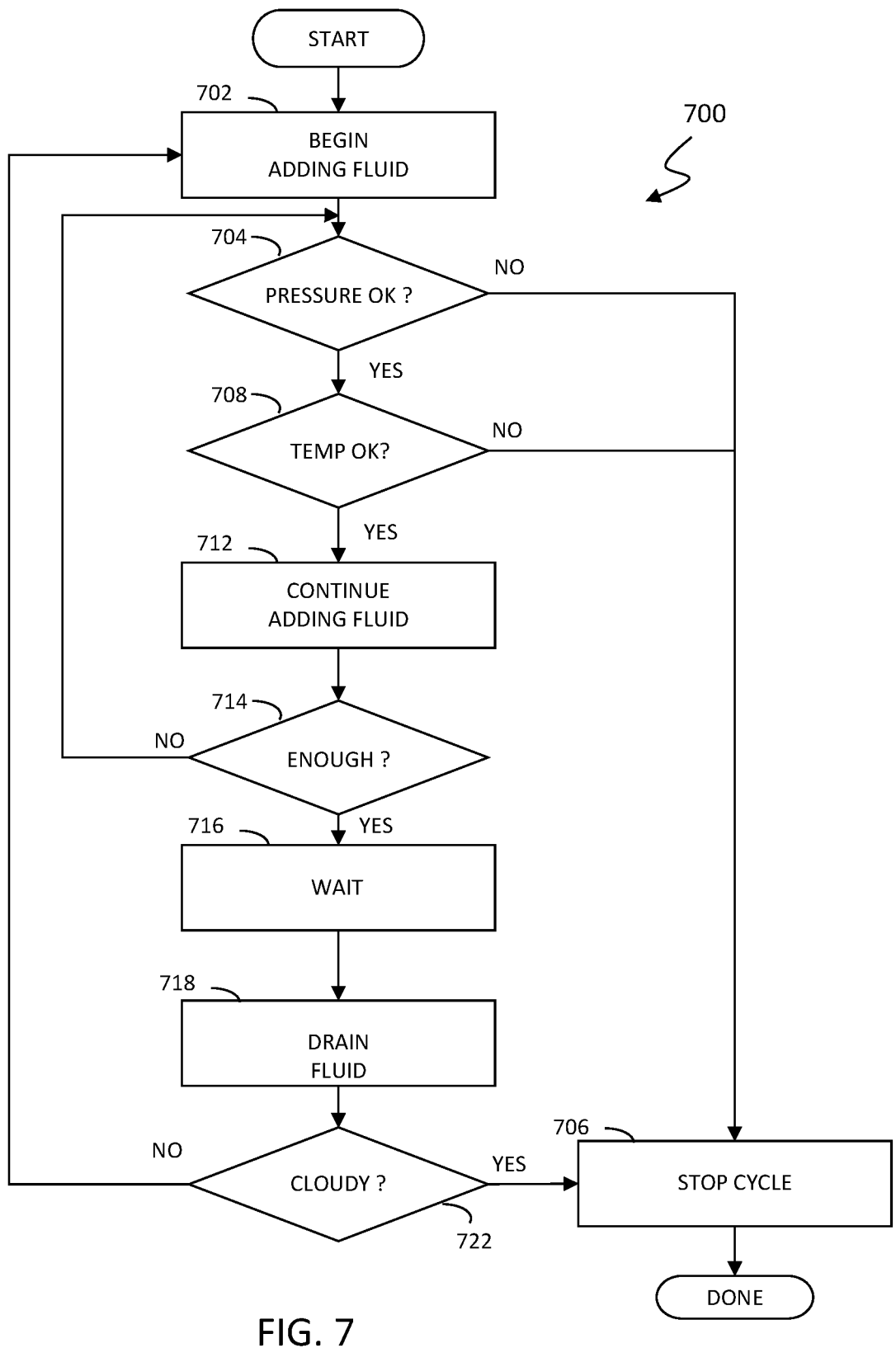
FIG. 7 is a flow diagram that illustrates operation of a dialysis machine with data from a sensor assembly in accordance with the present disclosure.

Referring to FIG. 7, a flow diagram 700 illustrates operation of the dialysis machine 102 using data from sensors on the sensor assembly 322 (or the sensor assembly 322', or similar). At a first step 702, the dialysis machine 102 begins filling the peritoneal cavity of the patient with dialysate. Following the step 702 is a test step 704 where it is determined if the pressure of the fluid entering the patient (from a sensor of the sensor assembly 322) exceeds a predetermined value, indicating a possibly serious difficulty. If so, then control transfers from the test step 704 to a step 706 where the system stops cycling (i.e., stops filling the patient with fluid). Other operations that may be performed at the step 706 include draining any remaining fluid from the patient, logging measurements from different sensors of the sensor assembly 322, sending an error message to appropriate medical personnel, etc. In an embodiment herein, audible alarms may be avoided in many instances because the patient is presumed to be sleeping. Following the step 706, processing is complete.

If it is determined at the test step 704 that the fluid pressure is OK (not too high), then control transfers from the test step 704 to a test step 708 where it is determined (using the sensor assembly 322, or similar) if the temperature of the fluid is OK (i.e., between 37 degrees C. and 41 degrees C.). If not, then control transfers from the test step 708 to the step 706, described above, where the system stops cycling.

Following the step 706, processing is complete. Otherwise, if it is determined at the test step 708 that the temperature is OK, then control transfers from the test step 708 to a step 712 where the dialysis machine 102 continues to add fluid. Following the step 712 is a test step 714 where it is determined is enough fluid has been added to the patient. If not, then control transfers from the test step 714 to the step 704, discussed above, for another iteration of testing and adding fluid. Otherwise, control transfers from the test step 714 to a step 716 where the system waits while the fluid in the patient remains in the patient to remove impurities.

Following waiting at the step 716 is a step 718 where the dialysis machine 102 causes the fluid to drain from the patient. Fluid that is drained from the patient flows in an opposite direction than when the fluid had been used to fill the patient. Following the step 718 is a test step 722 where it is determined (using the sensor assembly 322, or similar) if the fluid drained from the patient is cloudy, which could indicate an infection or other issue for the patient. If it is determined at the test step 722 that the fluid is cloudy, then control transfers from the test step 722 to the step 706, discussed above, where cycling is stopped. Following the step 706, processing is complete. If it is determined at the test step 722 that the fluid is not cloudy, then control transfers from the test step 722 back to the step 702 for another iteration of testing and adding fluid.

Implementations discussed herein may be combined with each other in appropriate combinations in connection with the system described herein. Additionally, in some instances, the order of steps in the flow diagrams, flowcharts and/or described flow processing may be modified, where appropriate. The system may further include a display and/or other computer components for providing a suitable interface with a user and/or with other computers. Aspects of the system described herein may be implemented or controlled using software, hardware, a combination of software and hardware and/or other computer-implemented or computer-controlled modules or devices having described features and performing described functions. Data exchange and/or signal transmissions to, from and between components of the system may be performed using wired or wireless communication. This communication may include use of one or more transmitter or receiver components that securely exchange information via a network, such as the Internet, and may include use of components of local area networks (LANs) or other smaller scale networks, such as WiFi, Bluetooth or networks using other short-range transmission protocols, and/or components of wide area networks (WANs) or other larger scale networks, such as mobile telecommunication networks.

Software implementations of aspects of the system described herein may include executable code that is stored in a computer-readable medium and executed by one or more processors. The computer-readable medium may include volatile memory and/or non-volatile memory, and may include, for example, a computer hard drive, ROM, RAM, flash memory, portable computer storage media such as a CD-ROM, a DVD-ROM, a memory card, a flash drive or other drive with, for example, a universal serial bus (USB) interface, and/or any other appropriate tangible or non-transitory computer-readable medium or computer memory on which executable code may be stored and executed by a processor. The system described herein may be used in connection with any appropriate operating system. The meanings of any method steps of the invention(s) described herein are intended to include any suitable method of causing one or more parties or entities to perform the steps unless a different meaning is expressly provided or otherwise clear from the context.

As used herein, an element or operation recited in the singular and preceded with the word "a" or "an" should be understood as not excluding plural elements or operations, unless such exclusion is explicitly recited. References to "one" embodiment or implementation of the present disclosure are not intended to be interpreted as excluding the existence of additional embodiments that also incorporate the recited features. Furthermore, a description or recitation in the general form of "at least one of [a], [b] or [c]," or equivalent thereof, should be generally construed to include [a] alone, [b] alone, [c] alone, or any combination of [a], [b] and [c].

Embodiments and implementations of the invention will be apparent to those skilled in the art from a consideration of the specification or practice of the invention disclosed herein. It is intended that the specification and examples be considered as exemplary only, with the true scope and spirit of the invention being indicated by the following claims.

What is claimed is:

1. A sensor assembly that is configured to measure characteristics of a fluid entering or exiting a patient via a catheter, comprising:
    a flow tube that is configured for coupling to a dialysis machine and to accept the fluid at a first end of the flow tube and expel the fluid at a second end of the flow tube;
    a tube-shaped docking station having a plurality of sensors disposed therein, the plurality of sensors including at least one IR temperature sensor that is external from a housing of the dialysis machine and configured to measure temperature of the fluid, at least one contact temperature sensor that is configured to measure temperature of the fluid, at least one clarity sensor that is configured to measure cloudiness of fluid from the patient, and at least one pressure sensor that is external from the housing of the dialysis machine and configured to measure pressure of the fluid, wherein information from the contact temperature sensor is combined with information from the IR temperature sensor to provide temperature measurement of fluid in the flow tube and wherein sensor information from the IR temperature sensor is given less weight when combined with information from the contact temperature sensor if information from the clarity sensor indicates that the fluid is cloudy; and
    a tube-shaped connector that is configured to be coupled to the docking station and is connected to the flow tube, wherein the docking station is provided in two parts that swing together on a hinge to close around the connector to couple the docking station to the connector.

2. The sensor assembly, according to claim 1, wherein the plurality of sensors further include at least one of: a conductivity sensor, a flow sensor, or an air detector.

3. The sensor assembly, according to claim 1, further comprising:
    a wireless communication device for providing wireless communication between each of the plurality of sensors and the dialysis machine.

4. The sensor assembly, according to claim 3, wherein the sensor assembly is configured to communicate with the dialysis machine via a network.

5. The sensor assembly, according to claim 3, wherein the flow tube is configured for coupling to a peritoneal dialysis machine.

6. The sensor assembly, according to claim 5, wherein the flow tube is configured for coupling to a dialysis machine that is configured to stop automatic cycling in response to at least one of: the temperature of the fluid exceeding a predetermined value or the pressure of the fluid exceeding a predetermined value.

7. The sensor assembly, according to claim 1, wherein the tube-shaped connector and the docking station include a coupling mechanism.

8. The sensor assembly, according to claim 7, wherein the coupling mechanism aligns particular sensors of the docking station with particular portions of the tube-shaped connector.

9. The sensor assembly, according to claim 8, wherein the coupling mechanism includes at least one of: a bar code, a chip, or physical features that align the tube-shaped connector with physical features of the docking station.

10. The sensor assembly, according to claim 9, wherein male and female portions of the physical features have a matching, interlocking pattern.

* * * * *